(12) United States Patent
Charron et al.

(10) Patent No.: US 7,468,513 B2
(45) Date of Patent: Dec. 23, 2008

(54) FAST DYNAMIC IMAGING PROTOCOL USING A MULTI-HEAD SINGLE PHOTON EMISSION COMPUTED TOMOGRAPHY SYSTEM

(75) Inventors: Martin Charron, Toronto (CA); Girish Bal, Philadelphia, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 168 days.

(21) Appl. No.: 11/155,086

(22) Filed: Jun. 17, 2005

(65) Prior Publication Data

US 2006/0000983 A1 Jan. 5, 2006

Related U.S. Application Data

(60) Provisional application No. 60/580,791, filed on Jun. 18, 2004.

(51) Int. Cl.
*G01T 1/166* (2006.01)
*G01T 1/161* (2006.01)

(52) U.S. Cl. .................. 250/363.05; 250/363.08; 378/10; 378/15

(58) Field of Classification Search ............... 250/394, 250/363.02, 363.04, 363.05
See application file for complete search history.

(56) References Cited

U.S. PATENT DOCUMENTS

| | | | |
|---|---|---|---|
| 4,196,352 A * | 4/1980 | Berninger et al. | 378/7 |
| 4,755,680 A | 7/1988 | Logan | |
| 5,444,252 A | 8/1995 | Hug et al. | |
| 5,471,061 A | 11/1995 | Moyers et al. | |
| 5,629,971 A | 5/1997 | Jones et al. | |
| 5,760,402 A | 6/1998 | Hug et al. | |
| 5,838,009 A * | 11/1998 | Plummer et al. | 250/363.05 |
| 6,150,662 A | 11/2000 | Hug et al. | |
| 6,242,743 B1 * | 6/2001 | DeVito et al. | 250/363.05 |
| 6,380,540 B1 | 4/2002 | Maor et al. | |
| 2003/0001099 A1 | 1/2003 | Coles et al. | |
| 2003/0004584 A1 | 1/2003 | Hallett | |
| 2003/0048937 A1 | 3/2003 | Gullberg et al. | |
| 2003/0108147 A1 | 6/2003 | Kojima et al. | |
| 2004/0195512 A1 * | 10/2004 | Crosetto | 250/363.04 |

OTHER PUBLICATIONS

Sitek et al., "Reconstruction of Dynamic Renal Tomographic Data Acquired by Slow Rotation", Journal of Nuclear Medicine, vol. 42, No. 11, Nov. 2001, pp. 1704-1712.
Celler et al., "Preliminary Results of a Clinical Validation of the Dspect Method for Determination of Renal Glomerular Filtration Rate (GFR)", IEEE MIC 2001, Oct. 2001, pp. 1079-1082.

* cited by examiner

*Primary Examiner*—David P Porta
*Assistant Examiner*—Casey Bryant
(74) *Attorney, Agent, or Firm*—RatnerPrestia

(57) ABSTRACT

An imaging system for acquiring multi-dimensional tomographic image data of an object, the imaging system having (1) a plurality of detectors to acquire image data, the detectors coupled to a supporting structure, wherein at least one of the detectors is adapted to move relative to the object during image data acquisition and wherein the detectors are adapted to rotate independently of each other, provided that image data from the detectors are collected concomitantly during a study time and (2) a data analyzer adapted to acquire and/or reconstruct the image data.

23 Claims, 3 Drawing Sheets

FAST DYNAMIC IMAGING PROTOCOL USING A MULTI-HEAD SINGLE PHOTON EMISSION COMPUTED TOMOGRAPHY SYSTEM

BACKGROUND OF THE INVENTION

1. Field of Invention

This invention relates to a field of nuclear imaging systems and in particular to medical nuclear imaging systems involving multiple gamma cameras.

2. Description of Related Art

Nuclear imaging systems had been widely utilized to obtained anatomic and physiological information about patients at the organ and tissue level. Recent studies showed enhancement of an observation scale to provide details of various tissues and their functions at increasingly microscopic levels.

Nuclear imaging systems emission computed tomography (ECT) and transmission computed tomography (CT). ECT is generally divided into two imaging techniques: single photon computed tomography (SPECT) and positron emission tomography (PET). ECT differs from CT in that in ECT the radiation source is a radioactive agent located inside the object (e.g., a patient) being imaged and in CT, the source of radiation is located outside of the object.

In ECT studies, the distribution of radioactivity in the object is measured after administration of the radioactive agent. The radioactive agents differ for SPECT and PET application such that PET studies require the use of positron-emitting radionuclides. For all nuclear imaging protocols, the amount of the radioactive agent is limited to that acceptable for the patient. This places further restriction on amount and activity of radiation available for detection since the radiation also attenuates in the object, which in turn affects the quality of image obtained. Especially for SPECT studies, wherein attenuation is more of a problem, improvements in obtaining better quality images are needed. The time for acquiring images depends on the activity of the radioactive agent or a tracer used in the study. For humans, it is important to keep such time at a minimum because of danger of radiation to one's health and also the inconvenience of being in a confined environment. To reduce the time of imaging study, multiple cameras or detectors or a multi-head imaging systems have been used.

Using commercially available multi-head SPECT imaging systems, it is possible to keep all heads stationary and acquire dynamic planar images (2D images) or to rotate all heads at the same time wherein these heads do not rotate independently of each other and acquire tomographic SPECT images (3D images).

U.S. Pat. No. 6,150,662 to Hug et al. discloses a medical imaging system comprising multiple gamma ray detectors capable of being positioned in variety of angular positions including a position wherein one camera is substantially parallel to another camera. U.S. Pat. No. 5,760,402 to Hug et al. discloses a dual head gamma camera having two rotating heads wherein one head can be held stationary, however, these heads do not move independently of each other. These systems would allow to keep one head stationary and move or rotate the other head (but not acquire projection data at the same time) to a desired position as described by Hug et al. (U.S. Pat. Nos. 5,760,402 and 6,150,662). However, these systems were not used for acquiring projections from both heads at the same time.

U.S. Pat. No. 5,444,252 to Hug et al. discloses a system for reducing the imaging time required to generate SPECT images. FIGS. 2A-2C depict two detectors having their image direction arrows oriented at 90 degrees to reduce the imaging time of a 180 degree scan to a ½ of the imaging time of a single head system because data is acquired from two stops simultaneously.

However, rotations described by patents to Hug et al. are just for pre-positioning the camera heads before acquiring data and not for imaging while in rotation. Thus using these systems, it is possible to acquire planar dynamic images of, for example, kidneys (or VOI) or dynamic SPECT images of, for example, kidneys (or VOI) but it does not provide for acquiring images simultaneously.

Simultaneous acquisition of multiple views has been studied; however none of the studies disclose acquiring static (2D) and tomographic (3D) images at the same time.

U.S. Patent Application No. 2003/0004584 A1 to Hallett discloses a gamma camera system having a user interface capable of simultaneous acquisition of multiple views during a single study. Using a dual detector camera for SPECT studies, simultaneous acquisition of a static planar, a dynamic planar, or a gated planar views is described. Further, the disclosed interface has an option of adding the selected static, dynamic, or the gated planar view. Examples of time intervals for data acquisition include 600-700 milliseconds and 20 seconds.

U.S. 2003/0001099 A1 to Coles et al., discloses a gamma camera system having a user interface capable of simultaneous acquisition of multiple views during a single study.

Both Hallet and Coles at al., stated that the planar study where one head is stationary and the ECT study where the second head moves cannot be performed simultaneously as such studies need different head movements.

U.S. Patent Application No. 2003/0048937 A1 to Gullberg et al. discloses a method for improving the resolution of a medical imaging device using factor analysis. This method is applicable to variety of imaging devices including SPECT. Gullberg et al. disclose collecting (1) dynamic images of a canine heart using 99m TC-teboroxime with a three-detector IRIX scanner (Marconi Imaging Systems, Inc., Cleveland, Ohio) to acquire transmission and emission projection data by slow rotation every 6 seconds for 18 minutes and (2) dynamic images resulting from a planar 99m TC-MAG3 renal study using an eCam system (Siemens, Hoffman Estates, Ill.), wherein the images were acquired every 5 seconds. Gullberg et al. do not describe using a stationary detector contemporaneously with rotating detectors. This application does not disclose acquiring 2D and 3D data concomitantly during the study time.

U.S. Patent Application No. 2003/0108147 A1 to Kojima et al. discloses a radiological imaging apparatus suitable for SPECT (and PET) examination as well as other imaging applications. This reference discloses using multiple detectors disposed around a cavity (a through-hole) wherein a source of radiation (a patient) is located. Multiple detectors are arranged in the radial, axial and circumferential direction of the cavity. The reference discloses using three or more radiation detectors simultaneously to enhance accuracy. Pairing-up detectors that are mounted about 180 degrees apart from each other with respect to the axial center of the through-hole is described. Kojima et al. do not describe using rotating detectors.

U.S. Pat. No. 6,380,540 B1 to Maor, et al. discloses a SPECT system and a PET system using emission detectors and transmission detectors simultaneously. The emission detectors revolve by at least 180 degrees.

U.S. Pat. No. 5,471,061 to Moyers et al. discloses a method and apparatus for producing radioactive transmission measurements to form a 2-D or a 3-D image with a point source of radiation for SPECT and PET applications, wherein the point source rapidly moves in a selected path around an object. In the apparatus, detectors are disposed in a cylindrical array to register radiation projected from all angles from the source.

U.S. Pat. No. 4,755,680 to Logan discloses a tubular radiation imaging apparatus for SPECT and PET imaging having detectors disposed in a cylindrical array.

U.S. Pat. No. 5,629,971 to Jones et al. discloses a gamma camera and a method for SPECT studies having multiple rotatable detectors (capable of collecting emission image data and transmission image data) and multiple line sources emitting radiation, wherein each detector is associated with a particular line source. The line sources are used to gather transmission data in generating attenuation correction maps.

The disadvantage of the planar images is that the counts from different organs may be superimposed. Currently available 3D images do not provide sufficient clarity and have a significant amount of noise. Using a tracer that has a fast disappearance rate, would not allow comparing static 2D and ECT 3D data if these studies were conducted sequentially and therefore require a repetitive exposure of a patient to an additional dose of radiation.

Another approach to imaging is a dynamic SPECT imaging in which data are acquired during a slow rotation of a camera using a standard tomographic protocol. In this method, a 4D image (a series of 3D) can be collected and each time-frame of such 4D image can be viewed as 2D or 3D as well as played as a 3D movie.

Sitek et al. conducted nuclear medicine renal study by measuring the clearance of radiopharmaceuticals from kidneys utilizing $^{99m}$Tc-mercaptoacetyltriglycyne (MAG3) (see Reconstruction of Dynamic Renal Tomographic Data Acquired by Slow Rotation JNM Vol. 42 No. 11, pp. 1704-1712). In the study, dynamic SPECT data acquisition was performed by slow rotation of detectors.

Similarly, Celler et al. disclose using the dynamic SPECT imaging (dSPECT) method for renal studies (see Preliminary results of a clinical validation of the dSPECT method for determination of renal glomerular filtration rate (GFR), presented at the IEEE MIC 2001, October 2001).

Thus, despite the foregoing developments, there is still a need in the art for nuclear imaging systems that can provide better resolution obtained in a reasonable amount of time and without the use of additional radiation. Further, there is a need for nuclear imaging systems which can provide quantitative imaging.

All references cited herein are incorporated herein by reference in their entireties.

BRIEF SUMMARY OF THE INVENTION

Accordingly, the invention provides an imaging system for acquiring multi-dimensional tomographic image data of an object, the imaging system comprising (1) a plurality of detectors to acquire image data, said detectors coupled to a supporting structure, wherein at least one of said detectors is adapted to move relative to the object during image data acquisition and wherein said detectors are adapted to rotate independently of each other, provided that image data from said detectors are collected concomitantly during a study time and (2) a data analyzer adapted to acquire and/or reconstruct the image data. In certain embodiments, the plurality of detectors comprises a first detector and a second detector, which do not maintain a constant angle relative to each other.

In this invention, we propose acquiring multi-dimensional images of the patient by keeping one head stationary and close to the patient and by rotating the other head such that they acquire 180 degree tomographic projections at the same time. Hence, this invention can combine the advantages of looking at dynamic planar images as well as 4D reconstructed images of the patient.

In certain embodiments, the first detector is positioned stationary in relation to the object to acquire planar two-dimensional data over a first period of time and the second detector is adapted to move relative to the object during image data acquisition to acquire three-dimensional data over a second period of time, provided that image data from the first detector and the second detector are collected concomitantly during the study time. In certain embodiments, the second detector is adapted to move with a variable speed. In certain embodiments, the second detector is adapted to move with a constant speed. In certain embodiments, the second detector has a starting position and a finishing position both located at an angle relative to the first detector, wherein the angle is selected such that the detectors do not collide with each other. For example, the angle can be from above 0 degrees to about 90 degrees. In certain embodiments, the second detector is rotating about the object from the starting position to the finishing position and from the finishing position to the starting position during image data acquisition. In certain embodiments, the second detector is making rotations of about 180 degrees.

In certain embodiments, said detectors are gamma ray detectors.

In certain embodiments, the multi-dimensional tomographic image data is a composition of planar two-dimensional data and three-dimensional data acquired concomitantly over a period of time.

Also provided is method for obtaining multi-dimensional tomographic image data of an object, the method comprising:
providing the imaging system of the invention;
providing an object; positioning the first detector stationary in relation to the object during data acquisition;
positioning the second detector adjacent to the first detector and rotating the second detector relative to the object during data acquisition; and
concomitantly collecting during a study time planar two-dimensional data acquired over the first period of time by the first detector and three-dimensional data acquired over the second period of time by the second detector; and thereby obtaining the multi-dimensional tomographic image data. In certain embodiments of the method, the second detector has a starting position and a finishing position both located at an angle relative to the first detector. In certain embodiments of the method, the second detector is making rotations of about 180 degrees.

Preferably, the second detector rotates from the starting position to the finishing position during the second period of time, wherein the second period of time is determined based on the kinetics of the tracer used. For example, the projection data from the multiple heads can be acquired either in seconds, for tracers with fast kinetics, or it might take few minutes for tracers with slow kinetics. In certain embodiments, the second period of time is less than eight seconds and in other embodiments, the second period of time is at most one second.

In certain embodiments, the object is a member selected from the group consisting of a kidney, a bladder, a pelvis, a bone, a lung, a thyroid, a brain and a heart.

Further provided is a method of determining a parameter of an object, the method comprising obtaining multi-dimensional tomographic image data using the imaging system of the invention and thereby determining the parameter of the object. In certain embodiments of the method, the three-dimensional data are used to make an attenuation map. In certain embodiments of the method, the parameter is a member selected from the group consisting of a renal filtration rate, a shape, a volume, and a location in a body.

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF THE INVENTION

Figure 1:
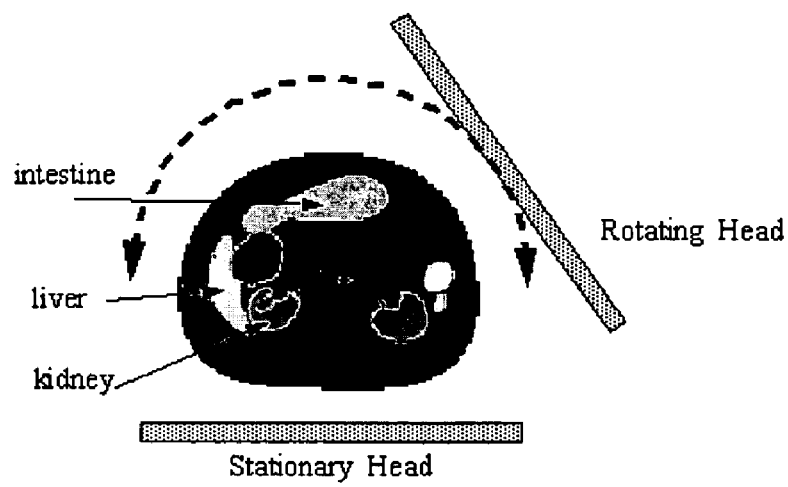
FIG. 1 is a schematic illustration of the imaging system of the invention showing the two-detector head SPECT system and a transaxial slice through a patient.
Figure 2:
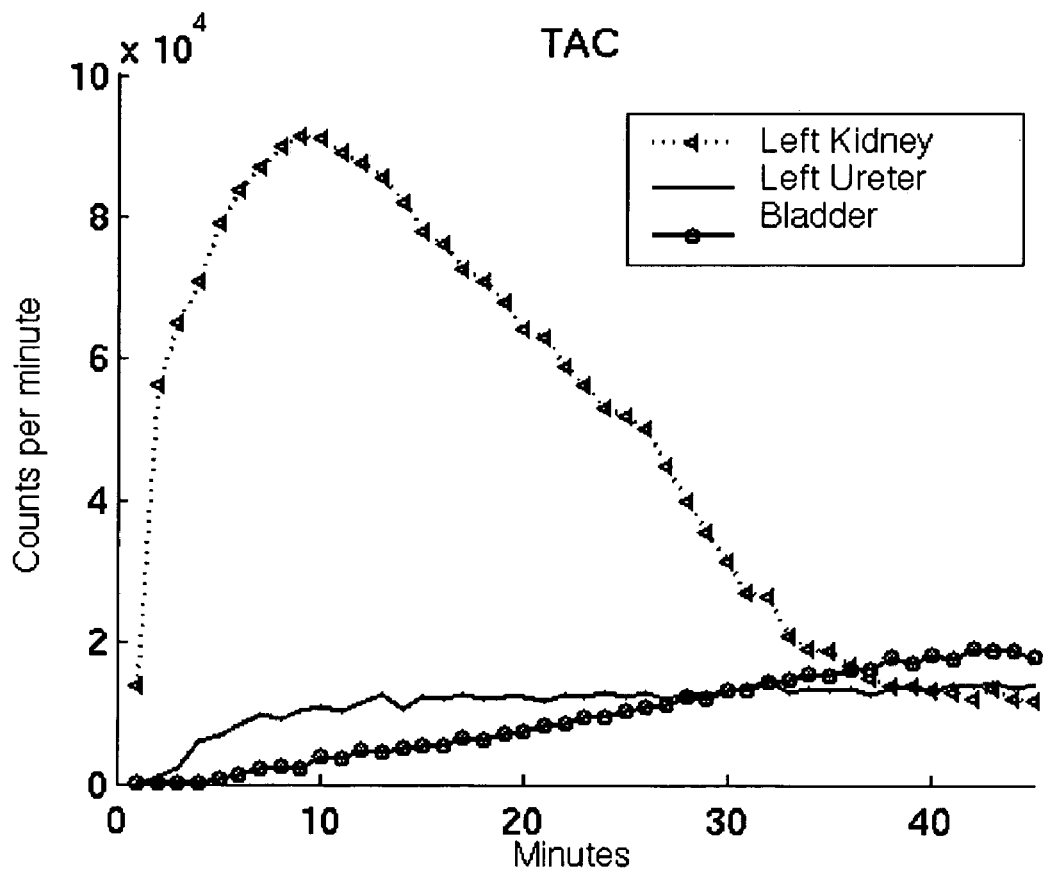
FIG. 2 is a graph illustrating time activity curves (for a stationary head only). A time activity curve (TAC) is obtained by selecting a region of interest in an image and finding how much intensity in present in that region in that minute. For example, the curve of the kidney will provide information regarding how much activity was sequentially present in the first minute, second minute, etc. In other words, TAC plot shows the dynamics of the tracer in the organ.
Figure 3:
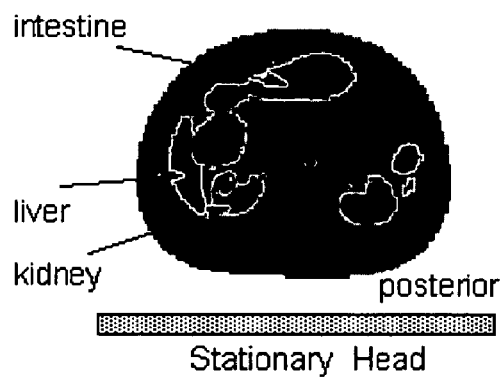
FIG. 3 is a schematic illustration of the imaging system used in prior art.

The invention was driven by a desire to develop a nuclear imaging systems capable of quantitative imaging that can provide better resolution obtained in a reasonable amount of time and without the use of additional radiation. The invention aims at improving the design and construction of the multi-head imaging single photon emission computed tomography (SPECT) system. This system can be used for screening natural (e.g., humans, animals, plants, etc.) and artificial objects, e.g., in nuclear medicine applications for screening or diagnosing. The invention is not limited to SPECT systems and can be used with PET and CT systems as well as other nuclear imaging systems.

The invention can be used for any applications where currently planar images are acquired, e.g., the study of obstructive uropathy, lung imaging, bone scans, imaging of the thyroid and brain. Now with multi-head scanners becoming very common the second and third head are literally lying idle or very little information is acquired using those heads. So this invention opens a wide range of possibilities where the planar images can be combined with tomographic information obtained from other heads to improve the prognosis and diagnosis of the disease.

In certain embodiments of the invention, the first detector is positioned stationary in relation to the object to acquire planar two-dimensional data over a first period of time and the second detector is adapted to move relative to the object during image data acquisition to acquire three-dimensional data over a second period of time, provided that image data from the first detector and the second detector are collected concomitantly during the study time.

In certain embodiments, 4-D dynamic images of an object (e.g., a patient or an organ) are collected utilizing at least two detector heads, wherein one detector head is held stationary and another detector head is rotating during the study and wherein acquiring data (projections) from both heads is conducted concomitantly as a set of consecutive projection collected over a specified period of time such as, for example, a set consisting of (a) projection collected by a stationary head, e.g., sixty projections (the number of projections can depending on the total detected counts, tracer dynamics, sensitivity of the system, etc.), wherein each projection is acquired during a one minute interval and (b) projection collected by a rotating head, e.g., sixty sets of individual projections, wherein each projection is acquired using a one second interval, the time during which the rotation from the starting position to the finishing position is completed. The acquisition time of the stationary and rotating head is varied depending on the total tracer injected to the patient, the sensitivity of the system and the dynamics of the tracer used.

4-D dynamic images are defined as a series of 3D reconstructed images obtained over time. Thus using the proposed method it is possible to study the tracer distribution in the patient as a sequence of 3D images, thereby enabling better diagnosis of the disease.

As used herein, "dynamic 3D data" means a sequence of 3D images in time (i.e., 4D images)

As used herein, "static 3D data" means the 3D reconstructed image obtained by summing up all the reconstructed 4D images mentioned above.

FIG. 1 demonstrates the imaging system of the invention utilizing two detector heads, wherein the stationary head is placed posterior to the object to be imaged and the rotating head is placed anterior to the object such that the rotating head is capable of being positioned at 90 degrees to the stationary head and also reach a parallel position while in rotation. Another inventive feature is a method of using the reconstructed 3-D SPECT image as the attenuation map, thus eliminating the need to expose the patient to an additional radiation. The imaging system of the invention can also use the attenuation map generated by an external transmission source or use the data from a CT image.

Figure 5:
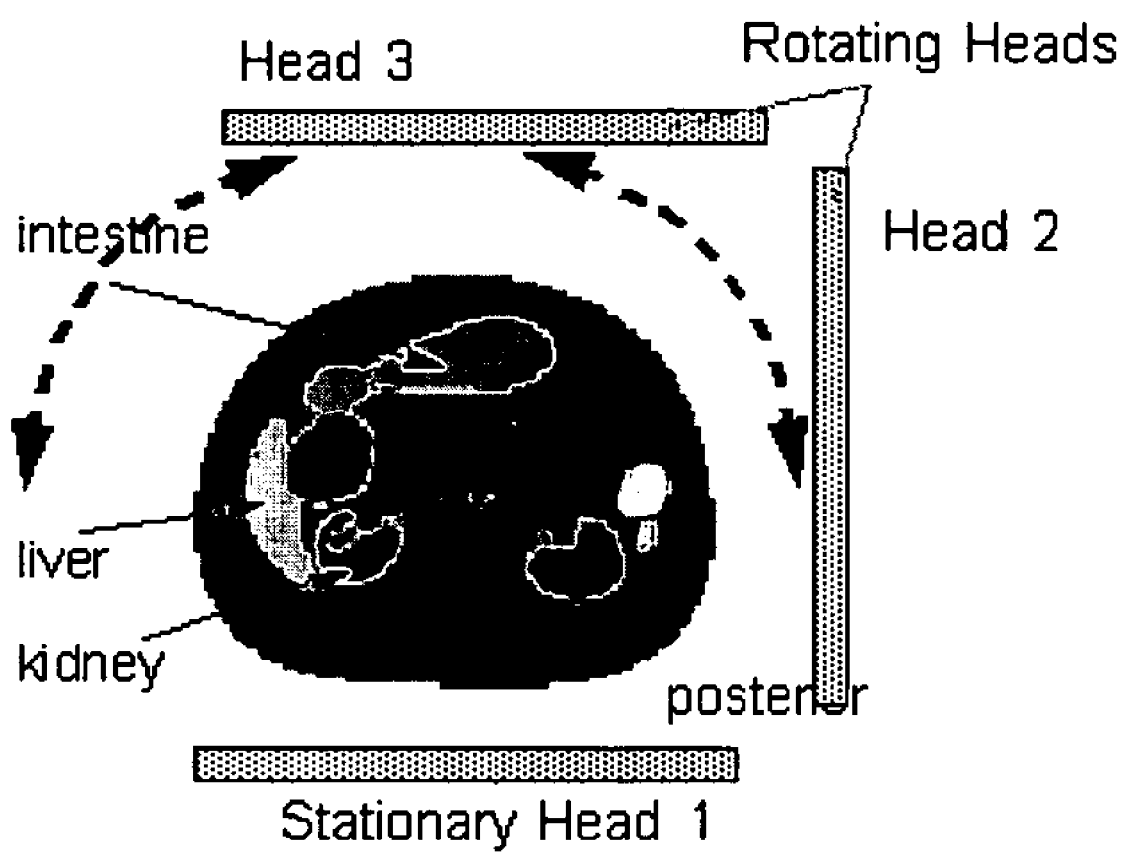
FIG. 5 is a schematic illustration of the imaging system of the invention showing a three-detector head SPECT system, wherein two heads are rotating and one head is stationary.

The two-head system can be easily extended to have more than two detectors, for example, as shown in FIG. 5. The data from a three head detector can be obtained by either placing one head stationary and rotating the other two heads or by keeping two heads stationary and rotating the third head. The rotating heads can be placed, for example, in the starting position at 90 degrees with respect to each other. In this case, the rotating heads needs to be rotated only by 90 degrees to move to the finishing position (and not 180 degrees as is the case with one rotation head in a two head embodiment) to obtain the complete data set. Then, the data from all three heads can be used in the image reconstruction. The rotating heads can be rotated at variable speeds relative to each other during the acquisition. The configuration shown in FIG. 5 is for illustration purposes, and the heads can be arranged in any other configuration.

In the invention, the dynamic 3D data are acquired using fast sampling. "Fast sampling" as used herein means that the rotating head or heads acquire sufficient data from the patient in a time period determined by the kinetics of the tracer used. For example for a Tc-99m MAG study performed on renal patients the 180 degree data can be acquired in just 5 seconds while for slower tracers it might take longer. This tracer kinetics dependent acquisition time results in a fast sampling of the tracer uptake as well as collecting precise tomographic information of the 3D volume. Further, it is now possible to compensate for image degradation factors such as attenuation and detector response function (DRF). Next, the combined data from all heads (static and rotating) were used to reconstruct the static 3D images of the patient's abdomen. This 3D static image provides a physician with a reference as well as information such as the exact volume of the kidney, pelvis, ureter, urinary bladder, depth of each kidney from the surface, etc. These accurate values can then be used to determine the various physiological parameters of the patient. This invention is an improvement over current technologies which use approximate values resulting in erroneous results. As discussed above, simultaneous acquisition of multiple views has been studied; however none of the studies disclose acquiring static (2D) and tomographic (3D) images at the same time, specifically, methods disclosed in prior art publications were not used to measure the planar dynamic images using the stationary head contemporaneously with a rotating head. Further, due to the slow sampling of the 3D volume, the acquired projections are inconsistent and cause artifacts in the reconstructed images. Advantageously, the simultaneous detection of the Volume of Interest (VOI) by multiple detectors results in a more faithful reconstruction. Further, since the second detector can be rotated at a fast rate (e.g., 180° in one minute), the reconstructed image would have much better quality and less inconsistencies arising from the fast dynamics of the tracer in the body.

Renal imaging is one of the areas in which the present invention can be used. Renal function involves excretory, regulatory and endocrine process in the body. Physiology of excretion is complicated as it involves filtration, reabsorbtion and secretion. Some major renal disorders imaged using SPECT are: obstructive uropathy, acute renal failure, renal infection, congenital anomalies, reflux nephropathy, and kidney transplant. Dynamic renal imaging usually consists of acquiring a series of one-minute planar images of a patient over a period of 40 to 45 minutes. However, the main limitations of this approach are 1) inability to measure quantitatively 4D distribution of the radiotracer 2) overlap of photons from different organs in the projections and 3) non-compensation of image degradation factors such as attenuation, detector response function (DRF) and scatter.

Drawbacks of the prior art approach include difficulties to differentiate between cortex and pelvis, absence of compensation for image degradation factors such as attenuation, DRF and scatter, background interference, results were not quantitative; and difficulties to determine the depth of kidney, thickness of the cortex and volume of the pelvis.

The method of the invention overcomes these limitations by enabling the acquisition of multi-dimensional tomographic images. The method comprises providing the imaging system of the invention, providing an object emitting or transmitting radiation, positioning the first detector stationary in relation to the object during data acquisition, positioning the second detector adjacent to the first detector and rotating the second detector relative to the object during data acquisition while keeping the first detector stationary, and concomitantly collecting during a study time planar two-dimensional data acquired over the first period of time by the first detector and three-dimensional data acquired over the second period of time by the second detector; and thereby obtaining the multi-dimensional tomographic image data. In certain embodiments of the method, the second detector has a starting position and a finishing position both located at an angle relative to the first detector, wherein the angle is from about 0 degrees to about 90 degrees. In certain embodiments of the method, the second detector is making rotations of about 180 degrees.

Preferably, the second detector rotates from the starting position to the finishing position during the second period of time, wherein the second period of time is less than eight seconds and more preferably, the second period of time is at most one second.

In certain embodiments, the object is a member selected from the group consisting of a kidney, a bladder, a pelvis, a bone, a lung, a thyroid, a brain and a heart.

The second period of time during which the second detector is rotating from the starting position to the finishing position is variable and depends on the kinetics of the tracer used. The acquisition time for the first detector and the second detector can vary from several hours to less than a second.

Inventors conducted a 45 minute simulated renal study using an extended NCAT phantom, consisting of the abdomen, kidney, pelvis, urether and bladder was generated. The dynamic uptake of the tracer by the different organs was modeled using measured time activity curves from a clinical renal scan of a normal subject injected with 10 mCi of $^{99m}$Tc-MAG3. Projection data were simulated as if one of the heads is stationary to acquire 45 projections of one minute each while the other head is rotated to acquire forty five sets of 180° acquisitions, consisting of 60 projections each acquired for 1 second. Thus, using this protocol, complete tomographic information as well as fast sampling of the radiotracer dynamics in the kidney s can be obtained. Finally, the dynamic projections from both heads were iteratively reconstructed, using a body contour defined uniform attenuation map, to give 45 reconstructed images corresponding to each minute of data acquisition.

A 45 minute planar and dynamic SPECT study was conducted in which attenuation, DRF and clinically equivalent noise levels were modeled. Reconstructed images were obtained.

From the above simulations, it was observed that noise is the primary limiting factor for 4D dynamic studies. However, due to the high extraction fraction of MAG3 by the kidneys, the observed noise levels were lower than those encountered in dynamic cardiac SPECT. The 4D reconstructed SPECT images were found to be similar to the phantom images used in the evaluation. Thus, the imaging system of the invention allows obtaining a faithful reconstruction with less bias and the improved quantitative information. The quantitative 4D images obtained using the fast sampling protocol combined with the planar dynamic projections, can improve the diagnosis of various renal disorders such as obstructive uropathy, differential function and mass lesions.

It was shown by Sitek et al. (2001) and Cellar et al. (2002) that dynamic renal imaging, using slow rotation of the gantry on a two or three head SPECT system, is possible. In these studies, the two or three head detectors were slowly rotated around the longitudinal axis of the patient, acquiring completed data, over a period of 20 to 30 minutes (i.e., slow sampling). This invention utilizes fast sampling, combined with dynamic planar imaging (such as, for example, the 30 second frames acquired post injection to see the initial blood input function, ROI analysis of the projection data, renogram of the projection images and split function analysis of each kidney) and dynamic renal imaging and therefore provides tomographic and temporal information of the 3D volume.

The projections from different organs were simulated separately, after modeling for physical degradation factors such as attenuation, detector response function and scatter. The dynamic uptake of the radiotracer was modeled, to get a set of inconsistent projections. The above steps were repeated for each organ and the projections of different organs were summed, to get the simulated dynamic projections from the abdomen. Clinically equivalent noise levels were then added to the projection data. For scanners capable of measuring the accurate attenuation map, the measured attenuation map is used during the reconstruction. For scanners that cannot measure the attenuation map of the patient, a 3D static SPECT image was first reconstructed using the combined projection data of the 40 minute study. Using the body contour of this 3D SPECT image, an attenuation map with uniform attenuation coefficients was generated for the reconstruction of the dynamic SPECT data. As the kidney lies in the abdomen, surrounded by soft tissue, this approach to use the approximate attenuation map would help to compensate for degradation in the image quality due to attenuation to a large extend.

The attenuation map obtained using this approach was found to be very close to the true attenuation map resulting in a faithful reconstruction of the dynamic SPECT images From the reconstructed image it was seen that quantitative dynamic renal images can be obtained using the fast sampling protocol mentioned above. Further, the high extraction fraction of radioisotopes such as MAG3 by the kidney helps to increase the count statistics of the projection data thereby making the fast one minute acquisitions clinically feasible. Inventors generated reconstructed 3D images that were quantitatively accurate. It is now possible to measure the volume and relative location of the kidney, pelvis and bladder with better precision than before. These measurements were then used in the calculation of physiological parameters such as the glomerular filtration rate (GFR), etc.

Figure 4:
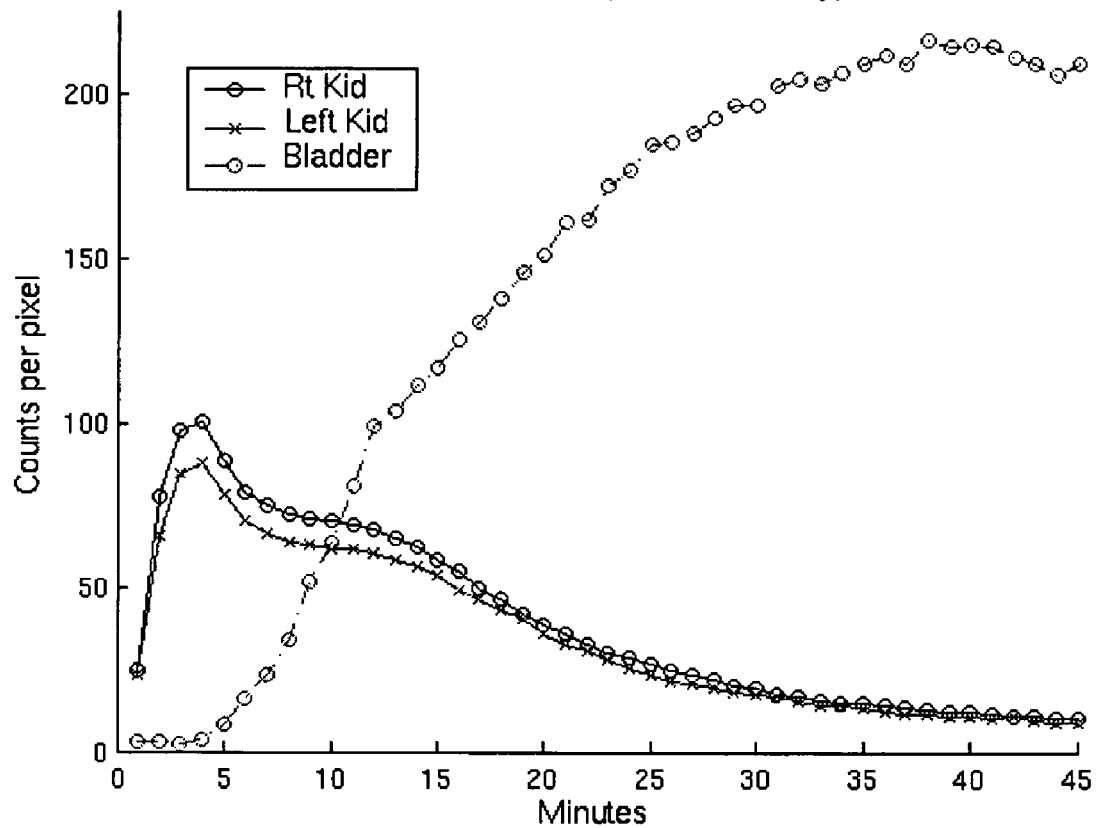
FIG. 4 is a graph illustrating normalized time activity curves (for the rat study).

Further studies using rats were performed to investigate the robustness of the imaging protocol as described below. Pilot rat study was conducted utilizing a system with a single pinhole with a diameter of 1 mm and 5 times magnification (see FIG. 4) wherein for the planar study 1 mCi TcMAG3 was injected and images were collected over a 45 minute study, and for dynamic study 6 mCi TcMAG3 was injected 1 hour later.

This invention can be applicable for imaging the dynamic uptake in any part of the body such as the heart, liver, brain etc. An unlimiting example of the imaging method of the invention is renal imaging as described below.

The novel dynamic imaging protocol for renal imaging includes the following steps: acquire dynamic planar projections from the VOI using one of the heads; acquire complete data from the VOI using the other head using fast rotation, combine all the projection data to obtain the 3D static image, use the data from the stationary planar head as well as from the rotating head to reconstruct 4D dynamic images of the patient, perform attenuation compensation using data from an attenuation map or using the boundary of the 3D image, and perform geometric response compensation modeling for the collimator used for more accurate quantification.

This invention improves currently used imaging methods by conferring the ability to compensate for image degradation factors such as attenuation, DRF and scatter and generate quantitative 4D images. Further, it makes possible to conduct a volumetric analysis by segmenting the high count 3D static image.

Further provided is a method of determining a parameter of an object, the method comprising obtaining multi-dimensional tomographic image data using the imaging system of the invention and thereby determining the parameter of the object. In certain embodiments of the method, the three-dimensional data are used to make an attenuation map. In certain embodiments of the method, the parameter is a member selected from the group consisting of a renal filtration rate, a shape, a volume, and a location in a body.

While the invention has been described in detail and with reference to specific examples thereof, it will be apparent to one skilled in the art that various changes and modifications can be made therein without departing from the spirit and scope thereof.

What is claimed is:

1. An imaging system for acquiring multi-dimensional tomographic image data of an object, the imaging system comprising:
   a plurality of detectors to acquire image data, said detectors coupled to a supporting structure, wherein at least one of said detectors is adapted to move relative to the object during image data acquisition and wherein said detectors are adapted to rotate independently of each other, provided that image data from said detectors are collected concomitantly during a study time; and
   a data analyzer adapted to acquire and/or reconstruct the image data.

2. The imaging system of claim 1, wherein a first detector and a second detector do not maintain a constant angle relative to each other.

3. The imaging system of claim 1, wherein the first detector is positioned stationary in relation to the object to acquire planar two-dimensional data over a first period of time and the second detector is adapted to move relative to the object during image data acquisition to acquire three-dimensional data over a second period of time, provided that image data from the first detector and the second detector are collected concomitantly during the study time.

4. The imaging system of claim 3, wherein the second detector is adapted to move with a variable speed.

5. The imaging system of claim 3, wherein the second detector is adapted to move with a constant speed.

6. The imaging system of claim 3, wherein the second detector has a starting position and a finishing position both located at an angle relative to the first detector, wherein the angle is variable provided that said detectors do not collide.

7. The imaging system of claim 6, wherein the second detector is rotating about the object from the starting position to the finishing position and from the finishing position to the starting position during image data acquisition.

8. The imaging system of claim 7, wherein the second detector is making rotations of about 180 degrees.

9. The imaging system of claim 1, wherein said detectors are gamma ray detectors.

10. The imaging system of claim 1, wherein the multi-dimensional tomographic image data is a composition of planar two-dimensional data and three-dimensional data acquired concomitantly over a period of time.

11. A method for obtaining multi-dimensional tomographic image data of an object, the method comprising:
   providing the imaging system of claim 1, wherein the first detector is positioned stationary in relation to the object to acquire planar two-dimensional data over a first period of time and the second detector is adapted to move relative to the object during image data acquisition to acquire three-dimensional data over a second period of time, provided that image data from the first detector and the second detector are collected concomitantly during the study time;
   providing the object;
   positioning the first detector stationary in relation to the object during data acquisition;
   positioning the second detector adjacent to the first detector and rotating the second detector relative to the object during data acquisition; and
   concomitantly collecting during a study time planar two-dimensional data acquired over the first period of time by the first detector and three-dimensional data acquired over the second period of time by the second detector; and thereby obtaining the multi-dimensional tomographic image data.

12. The method of claim 11, wherein the second detector is adapted to move with a variable speed.

13. The method of claim 11, wherein the second detector is adapted to move with a constant speed.

14. The method of claim 11, wherein the second detector has a starting position and a finishing position both located at an angle relative to the first detector, wherein the angle is variable provided that said detectors do not collide.

15. The method of claim 14, wherein the second detector is making rotations of about 180 degrees.

16. The method of claim 14, wherein the second detector rotates from the starting position to the finishing position during the second period of time, wherein the second period of time is less than eight seconds.

17. The method of claim 16, wherein the second period of time is at most one second.

18. The method of claim 11, wherein the object is a member selected from the group consisting of a kidney, a bladder, a pelvis, a bone, a lung, a thyroid, a brain and a heart.

19. A method of determining a parameter of an object, the method comprising obtaining multi-dimensional tomographic image data using the imaging system of claim 1, provided that the first detector is positioned stationary in relation to the object to acquire planar two-dimensional data over a first period of time and the second detector is adapted to move relative to the object during image data acquisition to acquire three-dimensional data over a second period of time, provided that image data from the first detector and the second detector are collected concomitantly during the study time; and thereby determining the parameter of the object.

20. The method of claim 19, wherein the three-dimensional data are used to make an attenuation map.

21. The method of claim 19, wherein the parameter is a member selected from the group consisting of a renal filtration rate, a shape, a volume, and a location in a body.

22. A method for acquiring multi-dimensional tomographic image data of an object, the method comprising the steps of:
positioning a first detector at a first detector position with respect to the object;
positioning a second detector at a second detector position with respect to the object, the second detector position being located at a different location than the first detector position;
rotating the first detector while maintaining the first detector in the first detector position;
maintaining the second detector stationary in the second detector position while the first detector rotates in the first detector position; and
simultaneously acquiring the multi-dimensional tomographic image data from the first and second detectors while the first detector is rotated and the second detector is stationary,
wherein the first detector is independently rotated to acquire a volume of interest (VOI) within the multi-dimensional tomographic image data.

23. The method of claim 22, further comprising the step of acquiring the multi-dimensional tomographic image data from a third detector located at a third detector position with respect to the object.

* * * * *